United States Patent [19]

Jung et al.

[11] Patent Number: 4,886,664

[45] Date of Patent: Dec. 12, 1989

[54] LOW-WATER-ACTIVITY INOCULA FOR BIOLOGICAL CONTROL

[75] Inventors: Gerard Jung, Montlhery; Jacques Mugnier, Lyon, both of France

[73] Assignee: Rhone-Poulenc, S.A., Paris, France

[21] Appl. No.: 502,244

[22] Filed: Jun. 8, 1983

[30] Foreign Application Priority Data

Jun. 18, 1982 [FR] France ................. 82 10636
Apr. 1, 1983 [FR] France ................. 83 05442
Apr. 1, 1983 [FR] France ................. 83 05443

[51] Int. Cl.⁴ .................... C12N 1/20; C12N 1/04; C12N 1/14; A61K 37/00
[52] U.S. Cl. ................... 424/93; 435/262; 435/254; 435/255; 435/260; 435/252.2; 435/253.3; 71/6; 71/7
[58] Field of Search ............ 424/34, 93; 435/253, 435/262, 272, 874, 877, 260, 878; 71/617

[56] References Cited

U.S. PATENT DOCUMENTS

| | | | |
|---|---|---|---|
| 1,909,622 | 2/1933 | Matchette . | |
| 2,901,864 | 7/1959 | Hiler | 47/ |
| 2,988,455 | 3/1961 | Rosenberg et al. | 106/169 |
| 2,995,867 | 5/1961 | Burton | 47/1 |
| 3,034,968 | 7/1962 | Johnston | 195/98 |
| 3,130,121 | 9/1964 | Rapport | 167/24 |
| 3,168,796 | 2/1965 | Scott et al. | 47/1 |
| 3,472,644 | 4/1969 | Woodside et al. | 71/1 |
| 3,616,236 | 10/1971 | Delin | 195/79 |
| 3,822,187 | 2/1974 | du Chaffaut et al. | 195/28 |
| 3,898,132 | 1/1975 | Hettrick | 195/65 |
| 4,038,140 | 7/1977 | Jaworek et al. | 195/63 |
| 4,089,746 | 8/1978 | Masri et al. | 195/63 |
| 4,146,706 | 8/1979 | Hisatsuka | 536/1 |
| 4,155,737 | 3/1979 | Dommergues et al. | 71/7 |
| 4,155,739 | 5/1979 | Dummergues et al. | 71/7 |
| 4,202,905 | 12/1980 | Asai et al. | 426/1 |
| 4,211,774 | 10/1980 | Kang et al. | 424/181 |
| 4,342,746 | 8/1982 | Strobel | 424/93 |
| 4,352,883 | 6/1982 | Lim | 435/178 |
| 4,376,113 | 1/1983 | Suglia et al. | 424/34 |
| 4,434,231 | 2/1984 | Jung | 435/253 |

FOREIGN PATENT DOCUMENTS

| | | |
|---|---|---|
| 521850 | 5/1953 | Belgium . |
| 977178 | 2/1975 | Canada . |
| 82402300 | of 1978 | European Pat. Off. ............ 435/253 |
| 1029839 | 2/1958 | Fed. Rep. of Germany . |
| 1103676 | 8/1955 | France . |
| 2469861 | 8/1981 | France . |
| 48-8830 | 3/1973 | Japan . |
| 628143 | of 1978 | U.S.S.R. . |
| 1177077 | 9/1967 | United Kingdom . |
| 1267685 | 11/1972 | United Kingdom . |
| 1526317 | 12/1978 | United Kingdom . |
| 1556584 | 2/1979 | United Kingdom . |

OTHER PUBLICATIONS

Jung et al., *Plant Soil*, vol. 65(2), pp. 219–231, "Polymer-Entrapped Rhizobium as an Inoculant for Legumes".
Beuchat, *Cereal Foods World*, vol. 26, pp. 345–349, 1981, "Microbial Stability as Affected by Water Activity".
Jung et al., including Diem, H. G., *Chem. Abst.*, vol. 97, 1982, No. 71457t, "Polymer-Entrapped Rhizobium as an Inoculant for Legumes".
Treybul, Robert, *Mass Transfer Operations*, 1980, McGraw Hill Book Co., N.Y., p. 697, lines 35–41.
J. Mugnier and G. Jung, *Applied and Environmental Microbiology*, Jul. 1985, vol. 50, No. 1, pp. 108–114.
Additional Abstract of Patrikeyev et al., Patent (Abstract 40,193).

(List continued on next page.)

*Primary Examiner*—Robin Teskin
*Attorney, Agent, or Firm*—Herbert F. Schwartz; Richard M. Barnes; Teresa L. Solomon

[57] ABSTRACT

A method of preparing inocula of low water activity is disclosed. The inocula are prepared by admixing microorganisms with a polymer gel and lowering and maintaining the water activity below 0.3, preferably below 0.1. These inocula are useful in the treatment of plant disease, particularly crown gall and Dutch elm diseases, as well as in the biological control of insects.

53 Claims, 4 Drawing Sheets

OTHER PUBLICATIONS

N. Amarger et al., "Influence of the Age of the Culture on the Survival of *Rhizobium meliloti* After Freeze Drying and Storage", 81 *Arch. Mikrobiol.*, 361–66 (1972).

G. Bond, "Some Reflections on Alnus-Type Root Nodules", *Recent Development in Nitrogen Fixation* (Newton, Postgate and Rodriquez-Barrueco eds., Academic Press 1977).

Ferron, "Biological Control of Insect Pests by Entomogenous Fungi", 23 *Ann. Rev. Entomol.*, 409–42 (1978).

M. Fraser, "A Method of Culturing *Rhizobium meliloti* on Porous Granules to form a Pre-Inoculant for Lucerne Seed", 39 *J. Appl. Bact.*, 345–51 (1975).

J. Graham et al., "Ethylene Production by Ectomycorrhizal Fungi, *Fusarium Oxysporum* f.sp. pini, and by Aseptically Synthesized Ectomycorrhizae and Fusarium-Infected Douglas-Fir Roots", 26 *Can. J. Microbiol.*, 1340–47 (1980).

G. Hunt et al., "Preservation of Cultures by Drying on Porcelain Beads", 76 *J. Bacteriology*, 453–54 (1958).

J. Janzen et al., "Specific Surface Area Measurements on Carbon Black", 44 *Rubber Chemistry and Technology*, 1287–96 (1971).

A. Kerr, "Biological Control of Crown Gall", *Waite Agricultural Research Institute, Biennal Report*, Universite of Adelaide, p. 4 (1975).

M. Lalonde et al., "Production of Frankia Hyphae and Spores as an Infective Inoculant for Alnus Species", *Symbiotic Nitrogen Fixation in the Management of Temperate Forests*, 95–110, (Proceedings of a Workshop Held at Oregon State University on Apr. 2–5, 1979).

M. Lalonde, "Confirmation of the Infectivity of a Free-Living Actinomycete Isolated from *Comptonia peregrina* Root Nodules by Immunological and Ultra-Structural Studies", 56 *Can. J. Bot.*, 2621–35 (1978).

D. Marx, "The Influence of Ectotrophic Mycorrhizal Fungi on the Resistance of Pine Roots to Pathogenic Infections II", Production, Identification, and Biological Activity of Antibiotics Produced by *Leucopaxillus cerealis* var. piceina, 59, *Phytopathology* 411–17 (1969).

*Method For Evaluating Biological Nitrogen Fixation*, (F. Bergersen ed. 1980), p. 493.

F. Munevar et al., "Growth of *Rhizobium japonicum* Strains at Temperatures Above 27° C.", 42 *Applied and Environmental Microbiology*, 272–76 (1981).

J. Pena-Cabriales et al., "Survival of Rhizobium in Soils Undergoing Drying", 43 *Soil Sci. Soc. Am. J.*, 962–66 (1979).

V. Patrikeyev et al., "Method of Producing Dry Microorganisms", 4, *Microbiology Abstracts: A Industrial Microbiology* A4153, (1969).

A Quispel, "Symbiotic Nitrogen Fixation in Non-Leguminous Plants", 9, *Acta Botanica Nèerlandica*, 380–96 (1960).

M. Salema et al., "Death of Rhizobia on Inoculated Seed", 14, *Soil Biol. Biochem.*, 13–14, (1982).

L. Siemaszko, 5(1), *Ann. Zool. Ecol. Anim.*, 69–75, (1973).

I. Takata et al., "Screening of Matrix Suitable for Immobilization of Microbial Cells", 2(3), *J. Solid-Phase Biochem.*, 225–36, (1977).

Anand et al., 64 (2), *American J. Botany*, 153–58, (1977).

Catroux et al., 2, *Ann. Zoologie Et Ecologie Animale*, 281–94, (1970).

D. Dye, 7, *Commercial Hort.*, 5–7, (1975).

A. Kerr, "Biological Control of Crown Gall: Seed Inoculation", 35, *J. Appl. Bact.*, 493–97, (1972).

Vincent, "A Manual for Practical Study of Root Nodule Bacteria", 215, *IBP Handbook*, 169, (Blackwell Scientific Publications, Oxford), *Phytom. Defenses des Cultures*, 43, (Jan. 1982).

LOW-WATER-ACTIVITY INOCULA FOR BIOLOGICAL CONTROL

The present invention relates to inocula for biological control and a method of preparing such inocula.

Plant and fruit cultures throughout the world are subject to serious diseases. For example, crown gall, a disease caused by *Agrobacterium tumefaciens*, affects numerous dicotyledons and results in large losses to nurseries and fruit cultures. The most serious losses are suffered by stone-fruit, apple, and pear trees, and by ornamental plants.

Because there are no efficient chemical controls against this disease, the economic problems resulting from losses of stock is particularly serious in regions that produce fruit or young plantlets. In addition to losses of stock, the problem is aggravated by laws restricting export of affected nursery stock. It has been estimated that the damage to stone-fruit trees alone was 138 million U.S. dollars in 1974.

Dutch elm disease, caused by *Ceratocystic ulmi* fungus, is another devastating and costly plant ailment. Since 1918, this disease has destroyed millions of elm trees. In the course of its life cycle, the disease-causing fungus assumes several forms (mycelium, spores that issue from the sprouting of a mycelium, conidiospores and ascospores), all of which are infectious to elm trees.

In addition to plant disease, insect infestation is another major problem for fruit and plant growers.

Chemical control of these diseases and of insects has so far proved inadequate. Furthermore, most chemical agents are not biodegradable and thus contribute to environmental pollution.

These problems underscore the importance of developing plant disease control methods other than by chemical methods, for example, biological control methods.

It is known to use preventively a strain of *Agrobacterium radiobacter var. radiobacter biotype* 2, referred to as "Strain 84" (or "K 84") for the efficient control of crown gall (A. Kerr, *J. Appl. Bact.*, 35, pp. 493–97 (1972)). This strain is marketed in the form of either a liquid culture (A. Kerr, *Waite Agricultural Research Institute, Biennal Report.*, University of Adelaide, p. 4 (1975)), a culture adsorbed on peat (D. Dye, *Commercial Hort.*, 7, pp. 5–7 (1975)), or in a petri dish unit package (*Phytom. Defenses des Cultures*, p. 43 (January 1982)).

Attempts have also been made to control the main vehicle of Dutch elm disese, that is, the coleoptera, with the aid of chemical or biological insecticides. Although treatment with these insecticides prevents progagation of the disease, it does not solve the problem of treating the elm trees that are already infected.

Attempts made to treat these trees have proved inadequate. U.S. Pat. No. 4,342,746 discloses treatment of the disease by using bacteria capable of developing in the sap of the elm tree and of producing a substance which strongly inhibits *Ceratocystis ulmi*. This biological treatment method has the advantage of preventing environment damage by using a microorganism, *Pseudomonas syringae*, which is not toxic to either humans or plants. To practice this method efficiently, however, large quantities of *Pseudomonas syringae* are required.

It has also been suggested that mixtures containing *Beauvaria bassiana* or *Metarhizium anisopliae* conidiospores be used for biological control of insects (Ferron, Biological Control of Insect Pests by Entomogenous Fungi," *Ann. Rev. Entomol.*, 23, pp. 409–42 (1978)). These entomopathogenic fungus spores, and particularly the blastospores obtained from the same fungus, for example, by culturing in a liquid medium, are extremely sensitive to temperature and to desiccation. Although wet preparations of these blastospores have been obtained, they are sensitive to contamination and have a limited shelf life of only two months at a storage temperature of 4° C. or a very reduced shelf life at a temperature of 23° C. (L. Siemaszko, *Ann. Zool. Ecol. Anim.*, 5(1), pp. 69–75 (1973)).

Because of the storage problems with these wet preparations, different drying means have been attempted in order to improve the shelf life of these blastospores. For example, French Patent Application No. 72.35452, published under No. 2,202,159, discloses a process for preparing entomopathogenic preparations in which the blastospores are first fixed in an inert support having a silica base and then are dried in the presence of a protective blend comprising sodium glutmate, saccharose, and paraffin oil containing a polyoxyethylenated oleic glyceride. One drawback of this process is that the resulting preparations must either be stored at 4° C. or be vacuum or nitrogen packaged.

Despite the foregoing, there is still a need for microorganism-containing inocula which can be preserved indefinitely without use of special storage conditions. Until now, it has been difficult to store living organisms without incurring substantial losses. Although storage of almost any microorganism in a liquid medium is possible, storage must be at a maximum temperature of 4° C. and for only relatively short periods of time and contamination must be avoided. These restrictions raise numerous technical problems.

The various inocula described in the prior art which are useful in biological control contain, in addition to the microorganism, a large percentage of water and nutritive elements issued from the microorganism culture. Accordingly, these inocula are easily contaminated and unstable, even for a short period of time, at temperatures beyond 40° C. Thus, because these prior art inocula must be stored at low temperatures and because they have short shelf lives, their use is limited.

SUMMARY OF THE INVENTION

The method and inocula of the present invention overcome all of the aforementioned problems. The microorganism-containing inocula prepared according to the method of the present invention have long storage lives and improved resistance to temperature. In addition, these inocula are easy to handle and are biodegradable.

Broadly, in one aspect of the present invention, a durable inoculum is prepared by including a culture medium containing microorganisms in a polymer gel, lowering the water activity ($a_w$) of the resulting mixture below 0.3, preferably below 0.1, and maintaining the water activity of this reduced level.

In another aspect of the present invention, the new inocula are used in the biological control of plant diseases, in particular, crown gall and Dutch elm diseases, as well as in the biological control of insects.

BRIEF DESCRIPTION OF THE DRAWINGS

To facilitate further description of the invention, the following drawings are provided in which:

FIG. 1 shwos the survival rate of *Agrobacterium radiobacter* in inocula A (curve 1) and B (curve 2) as a function of $a_w$ after 15 days of storage at 28° C..

DETAILED DESCRIPTION OF THE INVENTION

The various inocula useful in biological control may contain any microorganism existing in unicellular or sporulated form. The inocula may thus comprise a bacteria or fungi which is selected as a function of the purpose to be served, that is, the disease to be treated or the action sought to be accomplished. For example, bacteria such as *Agrobacterium radiobacter* may be used in the biological control of crown gall, while *Pseudomonas syringae* may be used in the biological control of Dutch elm disease. In addition, inocula containing entomopathogenic fungi, such as *Beauvaria bassiana, Metarhizium anisopliae, Sorosporella uvella,* and *Beauvaria tenella* may be used in the preparation of biological insecticides.

The inocula prepared according to the present invention may be used, depending on the microoganism incorporated therein, as insecticides, fungicides, or bactericides. These inocula are particularly useful in the treatment of crown gall and Dutch elm diseases. European Patent Application No. 82.402300.6 discloses a method useful in preparing the inocula of the present invention comprising including the microorganisms in a polymer, preferably cross-linked. The preparation of these inocula when using a cross-linked polymer takes place in three stages: (1) a solution of the polymer and a suspension of the microorganism to be included therein are formed; (2) the polymer is cross-linked, at least in part, so as to include the microorganism in the polymer gel; and (3) the water activity is lowered. The method of that application involves modifying the availability of the water so as to block its caloric power as well as its solvation. It is the availability of the water, expressed in terms of water activity ($a_w$), which, when it reaches extremely low values, makes it possible to protect the microorganisms from the harmful effects of contaminants present in the solutes used in the medium, as well as from the heat transfer capability of the water.

The water activity level below which the survival rate of microorganisms is at a maximum is a function of the constituents of the culture medium as well as of the polymer within which the microorganisms are incorporated. The critical water activity value below which all of these factors have a reduced effect has been discovered to be 0.3, and more effectively 0.1.

The water activity values are determined by a method known as Saturated Aqueous Solutions (Multon, "Techniques d'Analyse E De Controle Dans Les Industries Agroalimentaires", *APRIA* (1981)) or by direct measurement using a Rotronic BT hygrometer (hygroscope) (marketed by Richard and Pekly).

The microorganisms used in the present invention are preferably selected from the following species: *Beauvaria bassiana, Metarhizium anisopliae, Sorosporella uvella, Beauvaria tenella, Pseudomonas syringae,* and *Agrobacterium radiobacter.*

The culture medium in which these microorganisms are incorporated contains at least one source of each of the following: hydrocarbons, mineral salts, and a nitrogen source. Growth factors may also be included.

The hydrocarbon source is selected from the group consisting of sugars, such as glycerol, sorbitol, saccharose, glucose, and fructose, alcohols, di- or polyglycosides, and polysaccharides. The concentration of the hydrocarbon source in the culture medium my vary from 10 to 30 g/l.

The nitrogen source can be of mineral origin, such as ammonium or potassium nitrate, or of organic origin, such as lysine, arginine, glycine, glutamate, or soluble corn or yeast extracts. The concentration of the nitrogen source in the culture medium may vary from 1 to 20 g/l.

The polymer of the present invention is subjected to an at least partial cross-linking treatment. By "at least partial cross-linking treatment: is meant a treatment which is capable of modifying the structure of the polymer, such as heat treatment, treatment with a metal salt, or treatment with another polymer.

So as not to pollute the environment, the polymer in which the microorganisms are incorporated must be biodegradable. Therefore, it is preferable to use polymers having a polysaccharide base. These polymers are rapidly biodegraded and readily release the microorganisms. In addition, the use of polymers having a polysaccharide base promotes the growth of the bacteria or of the fungus in the soil after innoculation. That is because (1) the size of the polysaccharide particles permits the best dissemination of microorganisms over the seed of plant-matter to be protected; (2) the polysaccharide powder is rapidly rewetted; and (3) the polyssaccharide adheres readily to the soil particles, seeds, portions of the plant, and/or insects.

Preferably, the polymer is selected from the group consisting of bacterial and vegetable polysaccharides. Polysaccharides of bacterial origin useful in the method of the present invention are obtained through the fermentation of a carbohydrate by a microorganism of the genus Xanthomonas or of the genus Arthrobacter or by fungi of the genus Sclerotium. Polysaccharides of vegetable origin useful in the method of the present invention can be obtained from various sources of diverse origin, such as algae (alginates, carrageenans), plant exudates (karaya gum, tragacanth gum), and seeds (guar, carob bean).

Cross-linking can be carried out, for example, in the case of the alginates, by metal salts (e.g., salts of calcium).

According to the method of the present invention, the microorganism-containing material to be mixed with the polymer can be the liquid culture or a concentrate obtained by centrifuging the culture.

In one preferred embodiment of the method, a culture medium is prepared and seeded with a microorganism strain. After a few days of incubation, the culture medium is centrifuged and the total culture, spores, or bacteria obtained thereby are mixed with the polymer. The polymer in the suspension is subsequently cross-linked and the resultant gel is then dried.

The mixure of microorganism, polymer gel, mineral salt, hydrocarbon source, and nitrogen source in the culture medium constitutes between 2 and 10% of the suspension to be dried, on a dry-weight basis. The polymer represents between 1 and 2% of the suspension to be dried. Before drying, additives can be included in the suspension.

Drying consists of reducing the water activity below its critical value, that is, below 0.3, preferably below 0.1. Drying can be effected in various ways and in one or more steps. However, simply contacting the gel with air under ordinary conditions of temperature and relative humidity is not sufficient. Thus, a technique must be used which makes it possible to achieve more exhaustive drying. Examples of such a technique include: (1) contacting the gel with a dry, hot air stream, under conditions compatible with the survival of the microorganism and (2) complete air drying followed by dehydrating the powder obtained in a hermetically closed vessel containing a saturated solution of a compound having the required water activity, developing towards equilibrium with the inoculum. It should be understood that various drying techniques can be combined.

Preferably, a spray-drying technique is used. Unexpectedly, this technique was found to lead to inocula in which the survival of the microorganism is preserved even though the temperatures of the processing gases are far greater than those which the microorganism is normally capable of withstanding.

From an economic standpoint, it is preferable to use a two-stage drying system, such as that employed for the dehydration of milk. This system consists of a spray-drying stage which, when performed at a suitable temperature, results in a water activity in the inoculum on the order of 0.2 to 0.4, followed by a fluidized-bed stage which dries the inoculum to a water activity of less than 0.1.

The use of a two-stage drying system makes it possible to increase the rate of flow of the substance to be dried, and therefore also the difference in temperature between the inlet and outlet in the sprayer. The fluidized bed used to complete the drying and to attain a water activity below 0.1 consumes 2 to 4 times less energy for the removal of the last fraction of water than does spray-drying, thereby realizing an overall energy savings of approximately 20%.

The drying step is an important feature of the present invention because the drying methods used in the prior art lead to the destruction of the microorganisms.

To maintain the water activity at an optimum value during storage, a hermetic packaging method may be used, thereby limiting the transfer of water between the surrounding atmosphere and the internal atmosphere of the inocula.

The inocula of the present invention are available in the form of particles having a flexible structure rendering them ready for application either by dusting, suspending, or solubilizing in water, or by scattering on the soil or plants to be treated. Certain inocula, such as those having an Agrobacterium base or any entomopathogenic fungas base, can be provided on a support, for example, a support having a silica base.

If an absorbent such as silica is used, it can also perform a support and charge function, thereby facilitating the use and handling of the inoculum. Silica supports are preferably precipitated silica having a BET surface from 50 to 600 $m^2/g$. When a mineral charge having absorbent qualities such as silica is used, the allowable water activity is shifted toward higher values.

To further illustrate this invention, the following examples are provided. These examples are in no way meant to limit the scope of the invention.

Example 1

(1) Agrobacterium radiobacter Culture

The culture was developed for two days in a YEM A medium (as defined by Vincent, "A Manual for Practical Study of Root Nodule Bacteria," *IBP Handbook*, 215, p. 169 (Blackwell Scientific Publication, Oxford) having the following composition:

| Mannitol | 10 g/l |
| --- | --- |
| Difco yeast extract | 1 |
| $K_2HPO_4$ | 0.5 |
| NaCl | 0.2 |
| $MgSO_4.7H_2O$ | 0.2 |
| $FeCl_3$ | 0.004 |
| Water as needed to make | 1,000 |

The culture was also developed in a B medium (as defined by Anand et al., *American Journal of Botany*, 64 (2), pp. 153-58 (1977)) having the following composition:

| Saccharose | 10 g/l |
| --- | --- |
| Difco broth nutrient | 8 |
| Yeast extract | 1 |

The pH of the media was adjusted to 6.8 and the media were seeded with *Agrobactrium radiobacter* K 84 (Environmental Protection Agency - USA 38,087-2).

(2) Preparation of a Xanthan Polymer/Carob Flour Inoculum

Two solutions were prepared (the values are given for the preparation of 300 g of inoculum).

(a) Xanthan gum solution: a polysaccharide of the anionic type, having a molecule weight greater than $2 \times 10^6$, resulting from the fermentation of carbohydrates by a microoraganism of the genus Xanthomonas, will be referred to as "444Product 1."

To 100 ml of distilled water at a temperature of 70° to 80° C., 1.5 g of Product 1 were added. This temperature was maintained for 20 to 30 minutes, accompanied by stirring, and then lowered to between 40° and 50° C.

(b) Solution of the carob bean flour: a polysaccharide comprising D-mannopyranosyl units (1-4 bonds), one out of four or five being substituted at $C_6$ by D-galactopyranosyl having molecular weight of $3.1 \times 10^5$ will be referred to as "Product 2."

The same procedure was followed as in (a) above, with the exception that Product 1 was replaced with 1.5 g of carob bean flour.

When the two solutions reached 40° to 45° C., 50 ml of *Agrobacterium radidobacter* suspension were added to each of them, accompanied by constant stirring. The culture-xanthan gum mixture was then poured, with vigorous stirring, into the culturecarob bean flour mixture. A gel was obtained instantaneously.

Two types of inocula were obtained, A and B, depending on whether the suspension of bacteria from the culture medium A or B was used.

(3) Preparation of CaSO$_4$ - Alginate Polymer Inoculum

Preparation of this inoculum proceeded in two stages:

(a) Preparation of the Agrobacterium radiobacter suspension in an alignate having a viscosity between $150 \times 10^{-3}$ and $1,000 \times 10^{-3}$ Pa.s.

1 gram of alginate was dissolved in 80 ml of bacterial culture originating from culture medium A. Dissolution was accomplished by sprinking the alginate powder on the culture, with constant stirring, until the alginate powder was completely dissolved.

(b) Gelation

To the suspension of Agrobacterium radiobacter spores in the alginate were added 20 ml of a CaSO$_4$.2-H$_2$O solution having a concentration of 6 g/l. Solidification to a gel was instantaneous. This product will be referred to as "inoculum C."

In the examples that follow, the water activity of the inocula was controlled by means of saturated solutions. The water activities of the saturated solutions used are set forth below in Table 1:

TABLE 1

| SOLUTES (saturated solutions) | $a_w$ = Water Activity at 25° C. |
|---|---|
| Actigel (dehydrating compound) | 0.04 |
| NaOH | 0.07 |
| KC$_2$H$_3$O$_2$.1.5H$_2$O | 0.23 |
| CaCl$_2$.6H$_2$O | 0.31 |
| K$_2$CO$_3$.2H$_2$O | 0.43 |
| Ca(NO$_3$)$_2$.4H$_2$O | 0.51 |
| CuCl$_2$ | 0.68 |
| NaCl | 0.75 |
| KCl | 0.84 |

Figure 1:
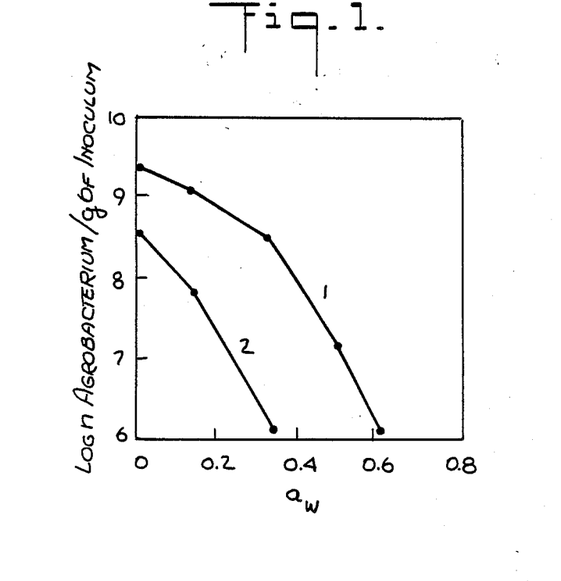

The survival of *Agrobacterium radiobacter* as a function of the water activity was plotted for two different inocula and is presented in FIG. 1. The curves of FIG. 1 illustrate that the survival of *Agrobacterium radiobacter* is at a maxium when the water activity of the inoculum is at a minimum. In addition, these curves indicate that the composition of the culture medium plays an important role in the survival of the bacteria. As demonstrated, the compounds of the culture medium contained in inoculum B are more damaging to the survival of the microorganism than those contained in inoculum A.

Figure 2:
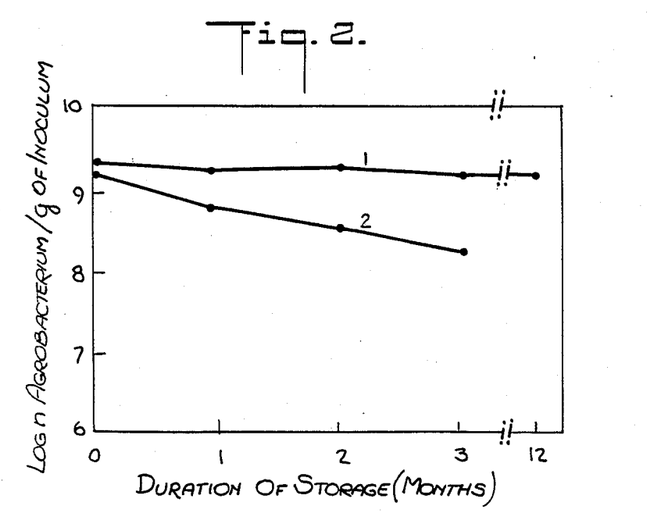
FIG. 2 shows the survival rate of *Agrobacterium radiobacter* in inoculum A stored at 28° C. as a function of time and of different values of $a_w$ (curve 1, $a_w=0.03$; curve 2, $a_w=0.11$)

FIG. 2 shows the survival rate of *Agrobcterium radiobacter* in inoculum A stored at 28° C. as a function of time and different values of $a_w$ (curve 1, $a_w$=0.03; curve 2, $a_w$=0.11). As illustrated, the survival of *Agrobacterium radiobacter* in a dehydrated biopolymer is possible for a storage period of at least one year.

Figure 3:
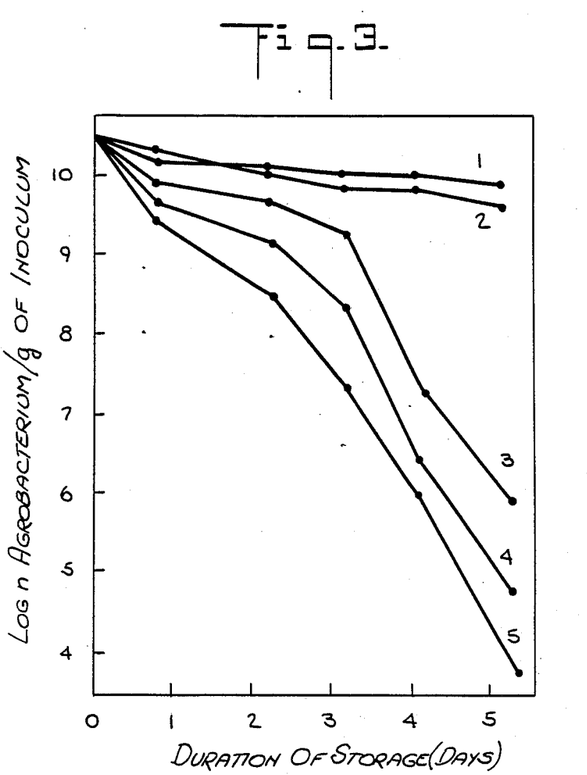
FIG. 3 shows the survival rate of *Agrobacterium radiobacter* in inoculum A stored at 55° C. as a function of time and of different values of $a_w$ (curve 1, $a_w=0.03$; curve 2, $a_w=0.07$; curve 3, $a_w=0.23$; curve 4, $a_w=0.31$; and curve 5, $a_w=0.43$)

FIG. 3 shows the survival rate of *Agrobacterium radiobacter* in inoculum A stored at 55° C. as a function of time and of different $a_w$ values (curve 1, $a_w$=0.03; curve 2, $a_w$=0.07; curve 3, $a_w$=0.23; curve 4, $a_w$=0.31, and curve 5, $a_w$=0.43). This figure illustrates the survival rate of the bacteria in the biopolymers at a relatively high temperature.

Figure 4:
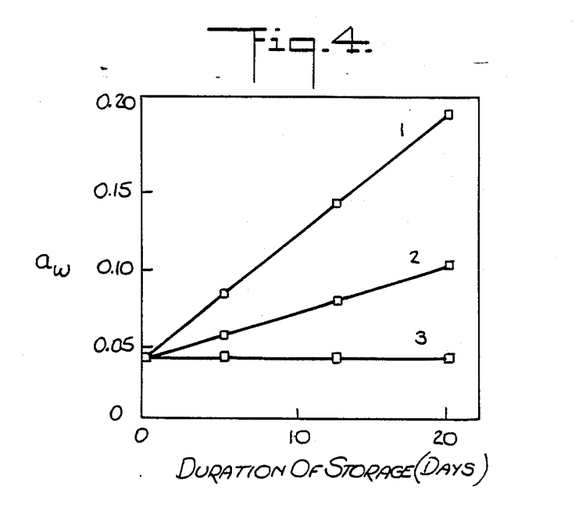
FIG. 4 shows the evolution of the $a_w$ in inoculum A stored at 38° C. with 90% relative humidity as a function of time and of different packaging materials (line 1=polypropylene package (RP films); line 2=metallized polypropylene packaging (RP films); line 3=metallized polyester-propylene packaging (Clarylene RP films)

FIG. 4 shows the evolution of the water activity in inoculum A stored at 38° C. and 90% relative humidity as a function of time and of the different packaging materials (line 1=polypropylene package (RP films); line 2=metallized polypropylene packaging (RP films); and line 3=metallized polyester-propylene packaging (Clarylene RP films)). The third type of packaging is impervious to water vapor. As illustrated by this figure, an airtight package is important in maintaining a low water activity value.

EXAMPLE 2

Table II illustrates a biological control test conducted by dusting inoculum A, which contained *Agrobacterium radiobacter* K 84, on a wound made at the base of tomato plant stems. The plants had been infected beforehand with a virulent *Agrobacterium tumefaciens* strain (C58 pTi C58, Phabagen Collection, Department of Molecular Cell Biology, De Mithof 3584 CH UTRECHT, The Netherlands).

TABLE II

Biological Control of Tomato Plants Infected With Crown Gall

| INOCULUM (*Agrobacterium tumefaciens*) | WEIGHT OF CROWN GALLS (g/plant) | | | | | | | | | | |
|---|---|---|---|---|---|---|---|---|---|---|---|
| C58 pTi C58 (0.2 ml liquid culture/plant) | 4.4 | 3.7 | 2.1 | 4.1 | 2.8 | 4.2 | 4.0 | 3.6 | 5.1 | 3.1 | 2.1 |
| C58 pTi C58 *Agrobacterium radiobacter* K 84 (liquid culture) 0.2 ml/plant | 0 | 0 | 0 | 0 | 0 | 0 | 0 | 0 | 0 | 0 | 0 |
| *Agrobacterium radiobacater* K 84 Inoculum A 2 mg/plant | 0 | 0 | 0 | 0 | 0 | 0 | 0 | 0 | 0 | 0 | 0 |

Age of the plantlets: 60 days.
The culture was incorporated on a vermiculite/perlite medium containing NPK and oligoelements.

As reported in Table II, the results of this test show that crown gall disease can be completely prevented with the use of inocula containing antagonisic bacteria incorporated in a dehydrated biopolymer.

EXAMPLE 3

In this example, the culture medium was seeded with the entomopathogenic fungus Beauvaria bassiana strain Bb 169 (INRA).

(1) Beauvaria bassiana Blastospore Culture

A culture of *Beauvaria bassiana* blastospores was grown over a period of five days in a basic medium of a soluble extract of corn/saccharose having the following composition (Catroux et al., *Ann. Zoologie et Ecologie Animale*, 2, pp. 281-94 (1970):

| | |
|---|---|
| Soluble corn extract | 20 g/l |
| Saccharose | 30 |
| $KNO_3$ | 5 |
| $KH_2PO_4$ | 6.8 |
| $CaCO_3$ | 0.2 |
| $MgSO_4.7H_2O$ | 0.1 |
| Water as needed to make | 1,000 |

(2) Preparation of a Xanthan Polymer/Carob Bean Flour Inoculum

This inoculum was prepared in the same manner as described in Example 1, with the exception that the *Agrobacterium radiobacter* suspension was replaced with a 50 ml suspension of *Beauvaria bassiana* spores.

(3) Preparation of an Alginate Polymer Inoculum

This inoculum was prepared in the same manner as described in Example 1, with the exception that the *Agrobacterium radiobacter* suspension was replaced with a suspension of *Beauvaria bassina* spores.

(4) Storage of the Gels Obtained

The resultant gels were air dried and subsequently placed in various vessels containing one of the saturated solutions listed in Table 1.

Figure 5:
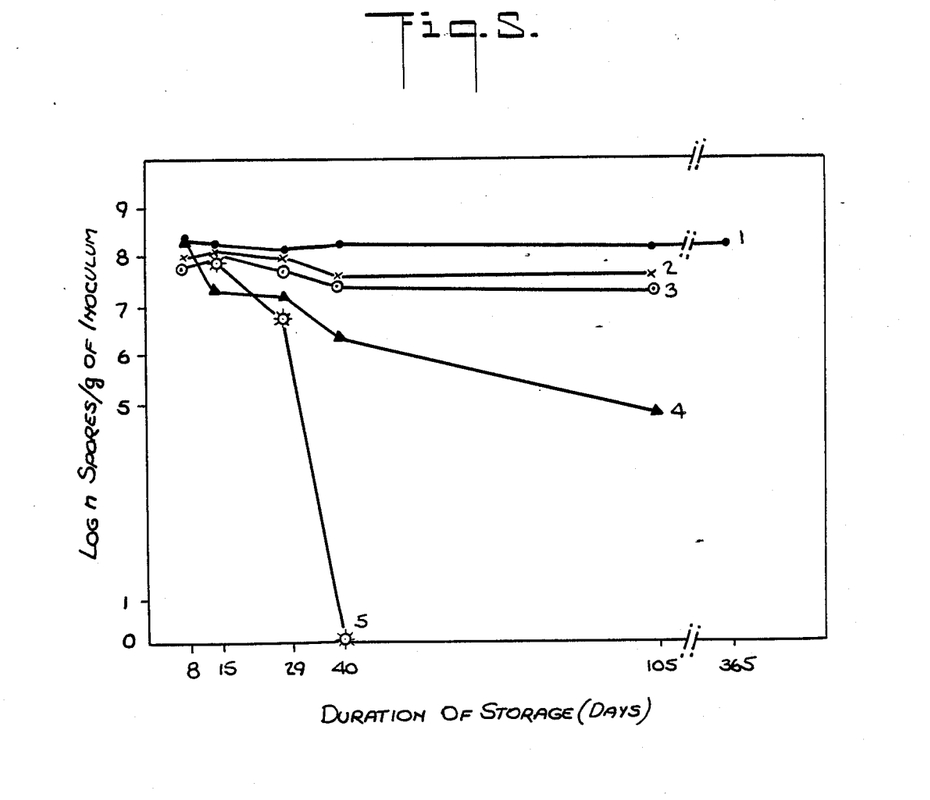
FIG. 5 shows the survival rate of *Beauvaria bassiana* blastospores included in a xanthan gum/carob beans flour gel as a function of time and different values of $a_w$ (curve 1, $a_w=0.07$; curve 2, $a_w=0.23$; curve 3, $a_w=0.31$; curve 4, $a_w=0.51$; curve 5, $a_w=0.68$)

FIG. 5 shows the survival rate of the *Beauvaria bassina* blastospores included in the abovedescribed inoculum as a function of time and of different values of $a_w$ (curve 1, $a_w=0.07$; curve 2, $a_w=0.23$; curve 3, $a_w=0.31$; curve 4, $a_w=0.51$; curve 5, $a_w=0.68$). As illustrated in FIG. 5, the survival rate of the blastospores is 100% when stored at 28° C. for one year at $a_w=0.07$. The loss of the blastospores is approximately 90% when stored at 28° C. for 100 days at the following higher values of $a_w$: $a_w=0.23$ and $a_w=0.31$.

Figure 6:
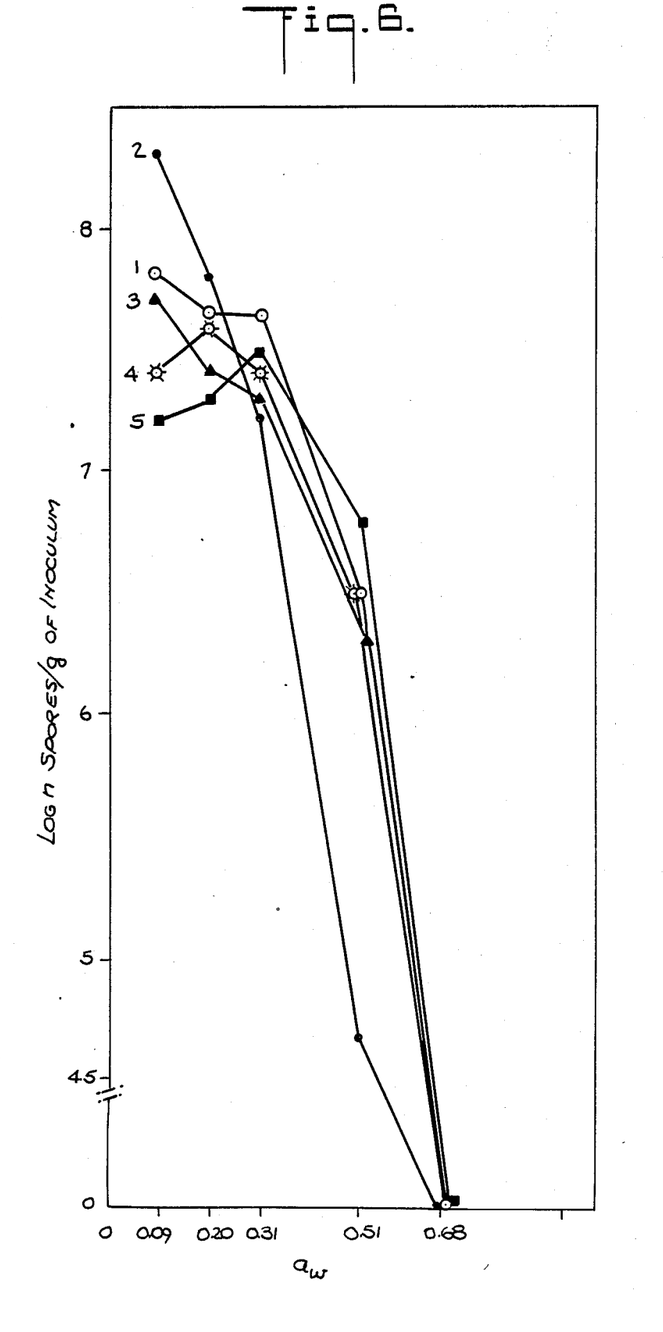
FIG. 6 shows the survival rate of *Beauvaria bassiana* blastospores included in alginate gels after (1) adding 10 to 40%, by weight, of a natural or synthetic silica gel, (2) drying, and (3) storing at 28° C. for 105 days, as a function of different values of $a_w$ (curve 1=addition of silica (I) to the culture; curve 2=spores without any additive; curve 3=spores30 FLO silica; curve 4=spores+silica (I); curve 5=spores+silica (II)).

FIG. 6 shows the survival rate of the *Beauvaria bassina* blastospores included in alignate gels following (1) the addition of 10 to 40%, by weight, of natural or synthetic silica gel, (2) drying, and (3) storing at 28° C. for 105 days, as a function of different values of $a_w$ (curve 1=addition of silica (I) to a culture of *Beauvaria bassina*; curve 2=spores without any additive; curve 3=spores+FLO silica; curve 4=spores+silica (I); curve 5=spores+silica (II)). The three types of silica used in this experiment are:

(1) a natural silica (Clarcel FLO silica having a perlite base);

(2) a precipitated silica (silica (I)), marketed under the trademark Zeosil 45, having the following characteristics and properties:
(a) a BET surface=250 $m^2/g$,
(b) oil capacity=320 $cm^3/100$ g, and
(c) CTAB=170 $m^2/g$; and (3) an experimental silica (silica (II)) having the following characteristics and properties:
(a) a BET surface=200 $m^2/g$,
(b) oil capacity=350 $cm^3/100$ g, and
(c) CTAB=90 $m^2/g$.

The CTAB surface (outer surface) of the silica additives was determined by adsorporation of cetyltrimethylammonium bromide at pH 9, according to the method described by J. Janzen et al., in *Rubber Chemistry and Technology*, 44, pp. 1287–96 (1971).

The presence of silica ensures survival of the *Beauvaria bassina* blastospores up to a water activity of 0.3, a marked improvement over gels containing the spores without any additives.

EXAMPLE 4

In this example, the culture medium was seeded with *Pseudomonas syringae* strain M 27 obtained from the Ortho Chemical Company. This strain has been filed with the Northern Utilization Research and Development Division under the number NRRL B 12050 and with the Institute Pasteur under the number I 142.

(1) Culture of Pseudomonas syringae

The culture was developed on gelose for three days. This culture was subsequently used to seed an Erlenmeyer flask containing 300 ml of YEM culture medium corresponding to the medium A, previously described in Example 1.

After incubation for three days at 28° C., the culture was used to seed an Erlenmeyer flask containing 2,000 ml the previously described YEM medium. Twenty-four hours later, a fermenting vessel containing 75 l of the same medium was seeded and the culture was also incubated for 24 hours. The number of bacteria resulting from this procedure was $3.2 \times 10^9$ bacteria/ml.

(2) Preparation of a Xanthan Polymer/Carob Bean Flour Inoculum

This inoculum was prepared in the same manner as described in Example 1, with the exception that the suspension of *Agrobacterium radiobacter* was replaced with a suspension of *Pseudomonas syringae*.

(3) Storage of the Gels Obtained

The gels obtained in this manner were air dried and subsequently placed in different vessels containing one of the saturated solutions listed in Table I. The logarithm of the number of surviving bacteria per gram, both before and after the drying stage was 9.3.

The dried *Pseudomonas syringae*-containing gels were subsequently stored for 90 days at 28° C. in vessels having the following water activities: 0.04, 0.07, 0.23, 0.31, 0.51, 0.75, and 0.84. After the 90-day period, the number of bacteria in the vessels was determined using the dilution-suspension method, a method known to those skilled in the art.

As summarized in Table III, the results of this experiment show that *Pseudomonas syringae* has an excellent survival rate if it is stored at a water activity below or equal to 0.07, and it has a reasonable survival rate if it stored at a water activity below 0.3.

TABLE III

| | Survival of *Pseudomonas syringae* as a Function of $a_w$ | | | | | | |
|---|---|---|---|---|---|---|---|
| $a_w$ | 0.04 | 0.07 | 0.23 | 0.31 | 0.51 | 0.75 | 0.84 |
| log n/g | 9.2 | 9.2 | 8.4 | 7.1 | 0 | 0 | 0 |

(4) Activity of Pseudomonas syringae on Ceratocystis ulmi

The activity of suspensions of *Pseudomonas syringae* was measured to estimate the inhibition of the growth of *Ceratocystis ulmi* in a Petri dish. The suspensions were obtained from a culture of *Pseudomonas syringae* incorporated in an alginate gel that had been dried, stored for 80 days at a water activity of 0.07, and then resuspended at a rate of 60 mg of dehydrated powder per 9 ml of solution (buffered at a pH of 7). The inhibition percentage of the culture reached 90% in comparison to a control suspension which was prepared in the same manner but which did not contain *Pseudomonas syringae*.

The activity level of *Pseudomonas syringae* on *Ceratocystis ulmi* was the same even after storage of 80 days at a water activity of 0.07.

(5) Effect of the Hydrocarbon Source on the Survival of Pseudomonas syringae

The survival of *Pseudomonas syringae* in culture media containing different hydrocarbon sources was also tested. The suspension of *Pseudomonas syringae* obtained above was subsequently included in an alginate gel that had been dried and then stored at 28° C. for 122 days at a water activity of 0.07. The number of surviving bacteria was determined using the dilution-suspension method. The culture medium which provided the optimum survival rate for *Pseudomonas syringae* was the YEM medium containing mannitol as the hydrocarbon source.

(6) Comparison of the Efficiency of Various Strains of Pseudomonas syringae on Ceratocystis ulmi The results of the efficiency of various strains of *Pseudomonas syringae* on *Ceratocystis ulmi* are summarized in Table IV below. The strains tested in this experiment were supplied by the Ortho Chemical Co., Institut National de la Recherche Agronomique Collection Nationale de Bacteries Phytopathogenes (C.N.B.P.).

TABLE IV

Effect of Various Strains of *Pseudomonas syringae* on *Ceratocystis ulmi*

| Strains of Pseudomonas syringae | Number of bacteria per ml | Inhibition of C. ulmi (%) |
|---|---|---|
| Chevron M 27 | $2.5 \times 10^9$ | 90 |
| INRA 62311 | $3.0 \times 10^9$ | 0 |
| INRA 62224 | $2.2 \times 10^9$ | 0 |
| INRA 64611 | $1.0 \times 10^9$ | 60 |
| INRA 5911 | $3.4 \times 10^9$ | 0 |
| CNBP 1585 | $1.9 \times 10^9$ | 80 |

We claim:

1. A storage-stable inoculum useful in biological control comprising:
    (a) a culture medium containing:
        (i) a microorganism selected from the group consisting of bacteria and fungi;
        (ii) a hydrocarbon source selected from the group consisting of sugars, alcohols, diglycosides, polyglycosides, and polysaccharides;
        (iii) a mineral salt; and
        (iv) a nitrogen source; and
    (b) a cross-linked biodegradable polymer; wherein the culture medium and biodegradable polymer have been admixed, subjected to a cross-linking treatment so as to at least partially cross-link the polymer, and dried to reduce the water activity to less than 0.3, said inoculum having a long storage life greater than 100 days when stored at 28° C.

2. The inoculum of claim 1 wherein the water activity is below 0.1.

3. The inoculum of claim 1 wherein the microorganism is *Agrobacterium radiobacter* K 84.

4. The inoculum of claim 2 wherein the microorganism is *Agrobacterium radiobacter* K 84.

5. The inoculum of claim 1 wherein the microorganism is *Pseudomonas syringae*.

6. The inoculum of claim 2 wherein the microorganism is *Pseudomonas syringae*.

7. The inoculum of claim 1 wherein the microorganism is an entomopathogenic fungus.

8. The inoculum of claim 2 wherein the microorganism is an entomopapthogenic fungus.

9. The inoculum of claim 7 wherein said entomoppathogenic fungus is selected from the group consisting of *Beauvaria bassina, Metarhizium anisopliae, Sorosporella uvella,* and *Beauvaria tenella.*

10. The inoculum of claim 8 wherein said entomopathogenic fungus, is selected from the group consisting of *Beauvaria bassina, Metarhizium anisopliae, Sorosporella uvella,* and *Beauvaria tenella.*

11. The inoculum of claim 1 wherein the polymer is a polysaccharide.

12. The inoculum of claim 2 wherein the polymer is a polysaccharide.

13. The inoculum of claim 1 wherein the polymer is partially cross-linked according to a method selected from thermal treatment, treatment with a metal salt, and treatment with another polymer.

14. The inoculum of claim 2 wherein the polymer is partially cross-linked according to a method selected from thermal treatment, treatment with a metal salt, and treatment with another polymer.

15. The inoculum of claim 1 wherein the polymer comprises xanthan gum and carob bean flour.

16. The inoculum of claim 2 wherein the polymer comprises xanthan gum and carob bean flour.

17. The inoculum of claim 1 wherein the polymer is an aliginate-base polymer.

18. The inoculum of claim 2 wherein the polymer is an alginate-base polymer.

19. The inoculum of claim 1 wherein the source of nitrogen is selected from the group consisting of ammonium nitrate, potassium nitrate, lysine, arginine, glycine, glutamate, soluble corn extract, and yeast extract.

20. The inoculum of claim 2 wherein the source of nitrogen is selected from the group consisting of ammonium nitrate, potassium nitrate, lysine, arginine, glycine, glutamate, soluble corn extract, and yeast extract.

21. The inoculum of claim 1 wherein the activity of the water is lowered by spray-drying.

22. The inoculum of claim 2 wherein the activity of the water is lowered by spray-drying.

23. The inoculum of claim 1 wherein the activity of the water is lowered by spray-drying followed by passage of the dried material over a fluidized bed.

24. The inoculum of claim 2 wherein the activity of the water is lowered by spray-drying followed by passage of the dried material over a fluidized bed.

25. The inoculum of claim 3 wherein the inoculum is provided on a support having a silica base.

26. The inoculum of claim 4 wherein the inoculum is provided on a support having a silica base.

27. The inoculum of claim 7 wherein the inoculum is provided on a support having a silica base.

28. The inoculum of claim 8 wherein the inoculum is provided on a support having a silica base.

29. The inoculum of claim 9 wherein the inoculum is provided on a support having a silica base.

30. The inoculum of claim 10 wherein the inoculum is provided on a support having a silica base.

31. The inoculum of claim 25 wherein the support comprises a precipitated silica having a BET surface area between 50 and 600 $m^2/g$.

32. The inoculum of claim 26 wherein the support comprises a precipitated silica having a BET surface area between 50 and 600 $m^2/g$.

33. The inoculum of claim 27 wherein the support comprises a precipitated silica having a BET surface area between 50 and 600 m²/g.

34. The inoculum of claim 28 wherein the support comprises a precipitated silica having a BET surface area between 50 and 600 m²/g.

35. The inoculum of claim 29 wherein the support comprises a precipitated silica having a BET surface area between 50 and 600 m²/g.

36. The inoculum of claim 30 wherein the support comprises a precipitated silica having a BET surface area between 50 and 600 m²/g.

37. The inoculum of claim 1, wherein said biodegradable polymer is a polysaccharide and is partially cross-linked using a method selected from the group consisting of thermal treatment, treatment with a metal salt, and treatment with another polymer, and said water activity is lowered by spray-drying.

38. The inoculum of claim 37, wherein said water activity is below 0.1.

39. The inoculum of claim 37, said inoculum being stable for at least one year when stored at 28° C.

40. An inoculum according to claim 1, wherein said microorganism is selected from the group consisting of bacteria and fungi that are useful in the biological control of insects or of plan diseases.

41. An inoculum according to claim 38, wherein said microorganism is selected from the group consisting of entomopathogenic fungi.

42. An inoculum according to claim 1, wherein said microorganism is *Agrobacterium radiobacter*.

43. An inoculum according to claim 38, wherein said microorganism is selected from the group consisting of bacteria and fungi that are useful in the biological control of insects or plant diseases.

44. An inoculum according to claim 38, wherein said microorganism is selected from the group consisting of *Agrobacterium radiobacter, Beauvaria bassina, Pseudomonas syringae, Metarhizium anisopliae, Sorosporella uvella,* and *Beauvaria tenella.*

45. A method of controlling plant diseases comprising applying to or near a plant an amount of a storagestable inoculum effective against crown gall disease or Dutch elm disease, said inoculum comprising:
(a) a culture medium containing:
  (i) a microorganism selected from the group consisting of *Agrobacterium radiobacter* , and *Pseudomonas syringae;*
  (ii) a hydrocabon source selected from the group consisting of sugars, alcohols, diglycosides, polyglycosides, and polysaccharides;
  (iii) a mineral salt; and
  (iv) a nitrogen source; and
(b) a cross-linked biodegradable polymer; wherein the culture medium and biodegradable polymer have been admixed, subjeced to a cross-linking treatment so as to at least partially cross-link the polymer, and dried to reduce the water activity to less than 0.3, said inoculum having a long storage life greater than 100 days when stored at 28° C.

46. A method according to claim 45, wherein said disease is crown gall disease and said microorganism is *Agrobacterium radiobacter* K84.

47. A method according to claim 46, wherein said water activity is below 0.1.

48. A method according to claim 45, wherein said disease is Dutch elm disease and said microorganism is *Pseudomonas syringae.*

49. A method according to claim 48, wherein said water activity is below 0.1.

50. A method of controlling insects in or on a plant comprising applying to or near a plant an amount of a storage-stable inoculum effective against insects, said inoculum comprising:
(a) a culture medium containing:
  (i) a microorganism selected from the group consisting of entomopapthogenic fungi;
  (ii) a hydrocarbon source selected from the group consisting of sugars, alcohols, diglycosides, polyglycosides, and polysaccharides;
  (iii) a mineral salt; and
  (iv) a nitrogen source; and
(b) a cross-linked biodegradable polymer; wherein the culture medium and biodegradable polymer have been admixed, subjected to a cross-linking treatment so as to at least partially cross-link the polymer, and dried to reduce the water activity to less than 0.3, said inoculum having a long storage life greater than 100 days when stored at 28° C.

51. A method according to claim 50, wherein said water activity is below 0.1.

52. A method according to claim 50, wherein said microorganism is selected from the group consisting of *Beauvaria bassina, Metarhizium anisopliae, Sorosporella uvella,* and *Beauvaria tenella.*

53. A method according to claim 52, wherein said water activity is below 0.1.

* * * * *

UNITED STATES PATENT AND TRADEMARK OFFICE
CERTIFICATE OF CORRECTION

PATENT NO. : 4,886,664

DATED : December 12, 1989

INVENTOR(S) : Jung et al.

It is certified that error appears in the above-identified patent and that said Letters Patent is hereby corrected as shown below:

Title Page/Abstract, column 2, line 6, change period to comma after "Dutch elm diseases."

Col. 2, line 60, Change "of" to -- at --.

Col. 3, line 1, Change "shwos" to -- shows --.

Col. 3, line 31, Change "30" to -- + -- (a plus sign).

Col. 3, line 54, Start new paragraph before "European."

Col. 4, line 31, Change "my" to -- may --.

Col. 4, line 41, Change ":" to -- " --.

Col. 4, line 56, Change "polyssaccharide" to -- polysaccharide --.

Col. 6, line 56, Change "molecule" to -- molecular --.

Col. 6, line 59, Delete "444" before "Product."

Col. 7, line 5, Change "radidobacter" to -- radiobacter --.

UNITED STATES PATENT AND TRADEMARK OFFICE
CERTIFICATE OF CORRECTION

PATENT NO. : 4,886,664

DATED : December 12, 1989

INVENTOR(S) : Jung et al.

It is certified that error appears in the above-identified patent and that said Letters Patent is hereby corrected as shown below:

Col. 7, line 8, Change "culturecarob" to -- culture-carob --.

Col. 7, line 17, Change "alignate" to -- alginate --.

Col. 9, line 24, Change "bassina" to -- bassiana --.

Col. 9, line 29, Change "bassina" to -- bassiana --.

Col. 9, lines 39-40, Change "bassina" to -- bassiana --.

Col. 9, line 45, Change "bassina" to -- bassiana --.

Col. 10, line 26, Add after "Inoculum," -- or an Alginate Polymer Inoculum --.

Col. 12, lines 5-6, Change "entomoppathogenic" to -- entomopathogenic --.

Col. 12, line 7, Change "bassina" to -- bassiana --.

Col. 12, line 11, Change "bassina" to -- bassiana --.

UNITED STATES PATENT AND TRADEMARK OFFICE
CERTIFICATE OF CORRECTION

PATENT NO. : 4,886,664
DATED : December 12, 1989
INVENTOR(S) : Jung et al.

It is certified that error appears in the above-identified patent and that said Letters Patent is hereby corrected as shown below:

Col. 13, line 39, Change "bassina" to -- bassiana --.

Col. 13, line 44, Change "storagestable" to -- storage-stable --.

Col. 14, line 29, Change "entomopapthogenic" to -- entomopathogenic --.

Col. 14, line 46, Change "bassina" to -- bassiana --.

Signed and Sealed this

First Day of February, 1994

BRUCE LEHMAN

*Attest:*

*Attesting Officer*      Commissioner of Patents and Trademarks